US005460603A

United States Patent [19]

DeSantis

[11] Patent Number: 5,460,603

[45] Date of Patent: Oct. 24, 1995

[54] METHOD AND APPARATUS FOR PREVENTING BACK FLOW IN GASTROENTEROLOGICAL FEEDING SYSTEM

[75] Inventor: Paul J. DeSantis, Saugus, Mass.

[73] Assignee: Massachusetts Institute of Technology, Cambridge, Mass.

[21] Appl. No.: 210,116

[22] Filed: Mar. 16, 1994

Related U.S. Application Data

[63] Continuation of Ser. No. 44,863, Apr. 8, 1993, abandoned.

[51] Int. Cl.$^6$ ..................... A61M 1/00

[52] U.S. Cl. ..................... 604/30; 604/54; 604/122; 604/126; 604/129; 604/247; 604/323; 604/324

[58] Field of Search ..................... 604/45, 30, 31, 604/49, 54, 83, 122, 126, 127, 129, 245, 247, 254, 256, 323, 324; 137/588

[56] References Cited

U.S. PATENT DOCUMENTS

| | | | |
|---|---|---|---|
| 4,160,383 | 7/1979 | Raushenberger | 73/422 |
| 4,315,513 | 2/1982 | Nawash et al. | 128/348 |
| 4,324,238 | 4/1982 | Genese et al. | 604/247 |
| 4,725,268 | 2/1988 | Ostensen et al. | 604/129 |
| 4,735,607 | 4/1988 | Keith Jr. | 604/54 |
| B1 4,863,438 | 1/1989 | Gauderer et al. | 604/247 |
| 4,941,875 | 7/1990 | Brennan | 604/83 |
| 4,944,732 | 7/1990 | Russo | 604/247 |
| 4,950,254 | 8/1990 | Andersen et al. | 604/247 |
| 5,073,166 | 12/1991 | Parks et al. | 609/93 |

OTHER PUBLICATIONS

Undated Brochure from Vent-Rite Valve Corp.

*Primary Examiner*—C. Fred Rosenbaum
*Assistant Examiner*—N. Kent Gring
*Attorney, Agent, or Firm*—Steven J. Weissburg

[57] ABSTRACT

Disclosed is an apparatus for providing liquid to a patient, preventing reflux and permitting venting. Tubes or other suitable apparatus are provided for connecting to the liquid source and the patient. An anti-reflux valve is provided in the hydraulic channel between the source and the patient. A vent is provided in the channel between the anti-reflux valve and the patient. Thus, gas urged from the patient under pressure is urged out of the vent. However, liquid similarly urged from the patient is prevented from overflowing by the anti-reflux valve. In a preferred embodiment, the anti-reflux valve is a flapper valve or a ball valve. In another preferred embodiment, the vent is a gas permeable, liquid impervious fabric. Alternatively, the vent may be a float valve. The invention is useful for gastroenterological feeding, nasogastric feeding and the like.

4 Claims, 4 Drawing Sheets

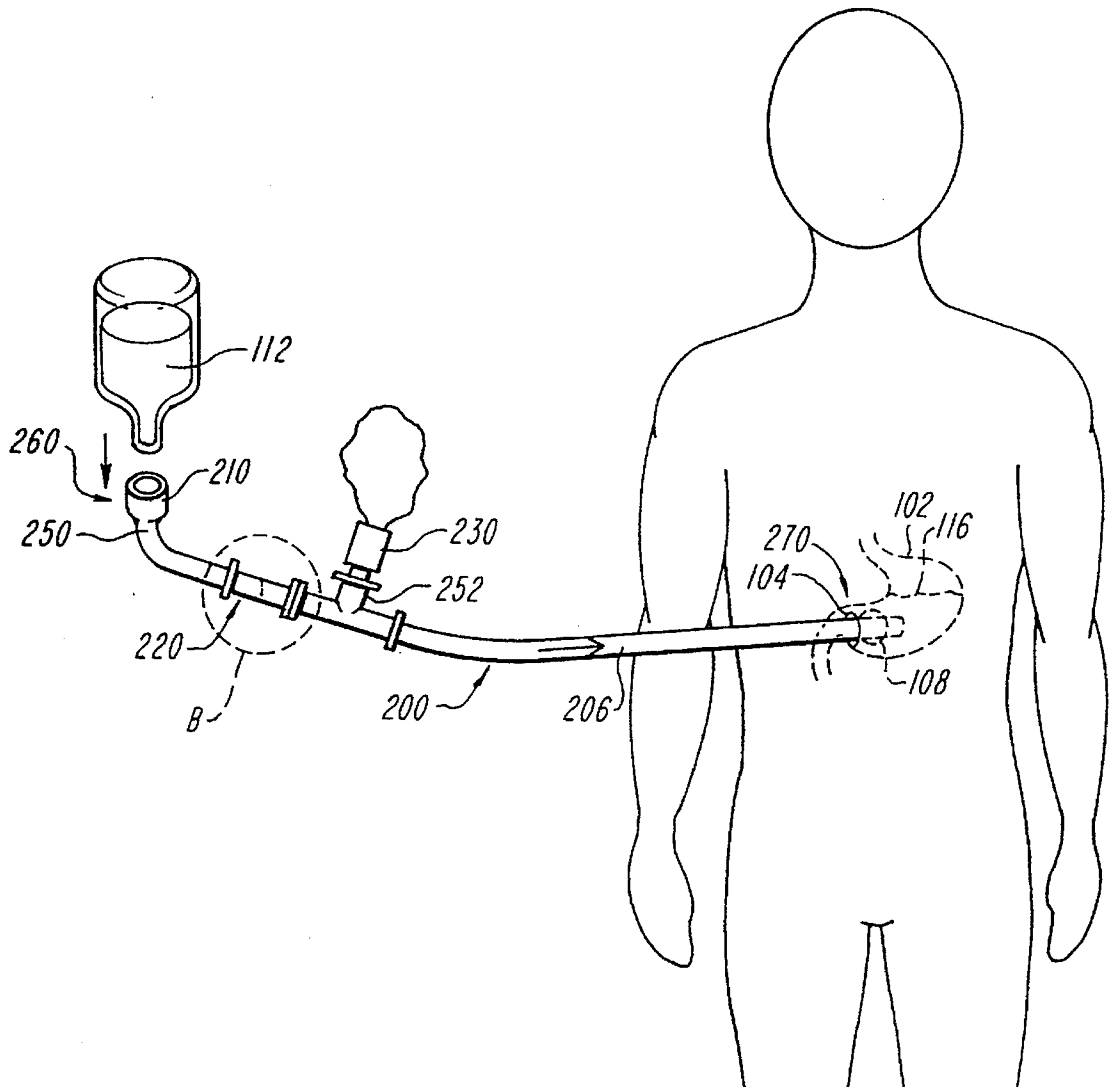
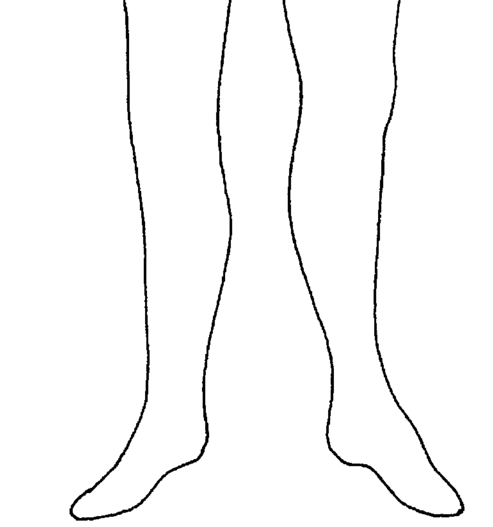
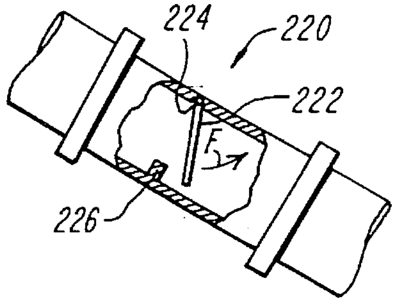
FIG. 2B
FIG. 2A

METHOD AND APPARATUS FOR PREVENTING BACK FLOW IN GASTROENTEROLOGICAL FEEDING SYSTEM

This is a continuation of application(s) Ser. No. 08/044,863 filed on Apr. 8, 1993, now abandoned.

The present invention relates generally to the medical field of introducing liquids, such as nutrients, medications and other treatments, to a mammalian subject, such as a human. It relates more specifically to the apparatus used to administer nutrients into the gastro-intestinal tract of a patient who cannot take nutrients as is normally done through the mouth. Most specifically, the invention relates to an apparatus for feeding patients gastroenterologically, which prevents reflux or back flow of stomach contents through the apparatus, yet also permits reduction of any pressure that may have built up inside the patient's body or the apparatus.

BACKGROUND

Various medical situations require the continuous or repeated introduction of substances, such as drugs or nutrients to bodily organs or tissues through a hole in a patient's skin, and organ walls (sometimes referred to as "percutaneous introduction"). As shown schematically in FIG. 1, typically, an appropriate tube 100 is introduced from outside the patient's body, through the skin, and into the organ 102 through an incision or surgical opening 104. The opening is referred to as a "gastrostomy." One such condition is a glycogen storage deficiency which requires the delivery of carbohydrates directly into the stomach. Another such condition is one where, for any of various reasons, the patient's normal esophogeal tract is inoperable, and nutrients must be provided directly into the stomach. Patients with tracheotomies often require such gastrostomical feeding, as well as patients with birth anomalies and other malformations.

A typical gastrostomy tube 100 is on the order of twenty five cm (10 inches) long and consists of a flexible tubing section 106, typically five to eight millimeters in diameter, made of a silicone composition that is physiologically inert. The end 130 that is inserted into the patient may have some sort of locking mechanism 108 to prevent its subsequent removal, such as an inflatable balloon that inflates to a size larger than the gastrostomy opening, or what is known as a Malecot tip.

The other, external end 120 of the tube is provided with an enlarged diameter section 110 for connection to the substance source 112. (To simplify discussion, the example of a nutrient supplied to the stomach will be used. However, the prior art and the invention apply to the introduction of other types of liquids, such as medications, testing dies, etc. to be applied to other organs or body cavities, and all are intended to be included in the invention.) The nutrient may be provided by a gravity feed mechanism, a pump, a syringe, or other devices.

Several problems arise in connection with the prior art devices. When nutrient is not being administered, the external end 120 must be closed off or kept gravitationally above the level 116 of liquid in the patient's stomach (or other organ system). Otherwise, if the external end 120 falls below the liquid level 116, liquid will be forced back out from the stomach out the tube and out of the external source end 120. This situation is obviously not desired. It is possible to clamp off the external end 120, so that even if the end falls below the liquid level 116, liquid will not leave the tube 106. A drawback to this solution is that pressure often builds up in the stomach (or other organ), due to the generation of gasses in the stomach, or due to muscular action, resulting from agitation or motion. Clamping off of the tube end 120 prevents relief of the building up pressure, further adding to the irritation, discomfort and pain of the patient.

The problem is particularly acute in connection with young children or infants who must be fed or administered with the gastrostomy tube. Such young individuals are unable, due to lack of maturity, comprehension, patience, etc., to take steps to minimize muscular agitation that increases pressure. Further, the more the pressure builds up, the more irritated or unhappy the young patient becomes, thus crying and fidgeting and tensing up more, causing more pressure, etc. Further, some patients are unable to relieve the buildup of stomach gas pressure through the esophogeal tract, such as by "burping", due to blockages or other problems with the esophogeal tract. Thus, the only path for expulsion of such built-up gasses is through the gastrological tube. The result is a cycle that builds and builds as pressure builds.

A common solution to such a problem is to "vent" the young patients by opening the external end 120, and fixing it above the liquid level 116. Fixing is commonly done by taping the free external end 120 to the patient's body above the liquid level, or to a part of the furniture or other surroundings in which they reside. Such "venting" tends to relieve the pressure for the young patients and calm them down.

A drawback of the venting method is that it results substantially in the demobilization of the patient. Further, if the taping becomes loose, the tube will fall and liquid will escape.

Another problem with known gastrostomy feeding apparatus occurs during feeding or introduction of liquid. Typically, liquid is introduced from a source 112 into the external end 120, and passes into the patient's body, either under the urging of gravity, or pressure established by a pump or syringe. However, even during feeding, the patient, particularly young patients, may become irritated to the extent that the pressure at the internal end 130 of the tube 100 exceeds the pressure at the external end 120, causing back flow or reflux of the contents of the stomach or other organ back out the tube. This presents many problems. It is undesirable for such liquid to mix with the fresh contents of the nutrient in bottle 112. However, if the source is disconnected from the tube 100, the back flowing nutrient will leak out causing a mess. Further, the nutrient is expensive, and attendants often try to save the back flowing nutrient, rather than simply draining it into a sink or other refuse receptacle. Even if the patient does not become agitated, the buildup of pressure from gas or other causes can cause a back flow problem.

OBJECTS

An object of the invention is to introduce liquids to a patient through a gastrostomy without the risk of back flow of liquids, and without the discomfort of increased pressure. Another object of the invention is to easily "vent" patients having gastrological tubes, without requiring taping an open-ended tube to an altitude higher than the liquid level in the stomach to prevent leakage. Another object of the invention is to enable feeding young or uncontrollably active patients without losing large quantities of nutrient or risking contamination of fresh nutrient with back flowing liquids. It is similarly an object to be able to provide medications and dyes to patients without the risk of back flow, while also permitting release of elevated pressure.

SUMMARY

A preferred embodiment of the invention is an apparatus for providing liquid to a patient, preventing reflux and permitting venting. Tubes or other suitable apparatus are provided for connecting to the liquid source and the patient. An anti-reflux valve is provided in the hydraulic channel between the source and the patient. A vent is provided in the channel between the anti-reflux valve and the patient. Thus, gas urged from the patient under pressure is urged out of the vent. However, liquid similarly urged from the patient is prevented from overflowing by the anti-reflux valve. In a preferred embodiment, the anti-reflux valve is a flapper valve or a ball valve. In another preferred embodiment, the vent is a gas permeable, liquid impervious fabric. Alternatively, the vent may be a float valve.

BRIEF DESCRIPTION OF THE FIGURES

These and other features, aspects, and advantages of the present invention will become better understood with regard to the following description, appended claims and accompanying drawings, where:

FIG. 2A shows schematically an overall view of the gastrological apparatus of the invention, having a gas vent and a liquid reflux barrier.

FIG. 2B shows enlarged the portion of FIG. 2A indicated at B.

DETAILED DESCRIPTION OF PREFERRED EMBODIMENTS

Figure 1:
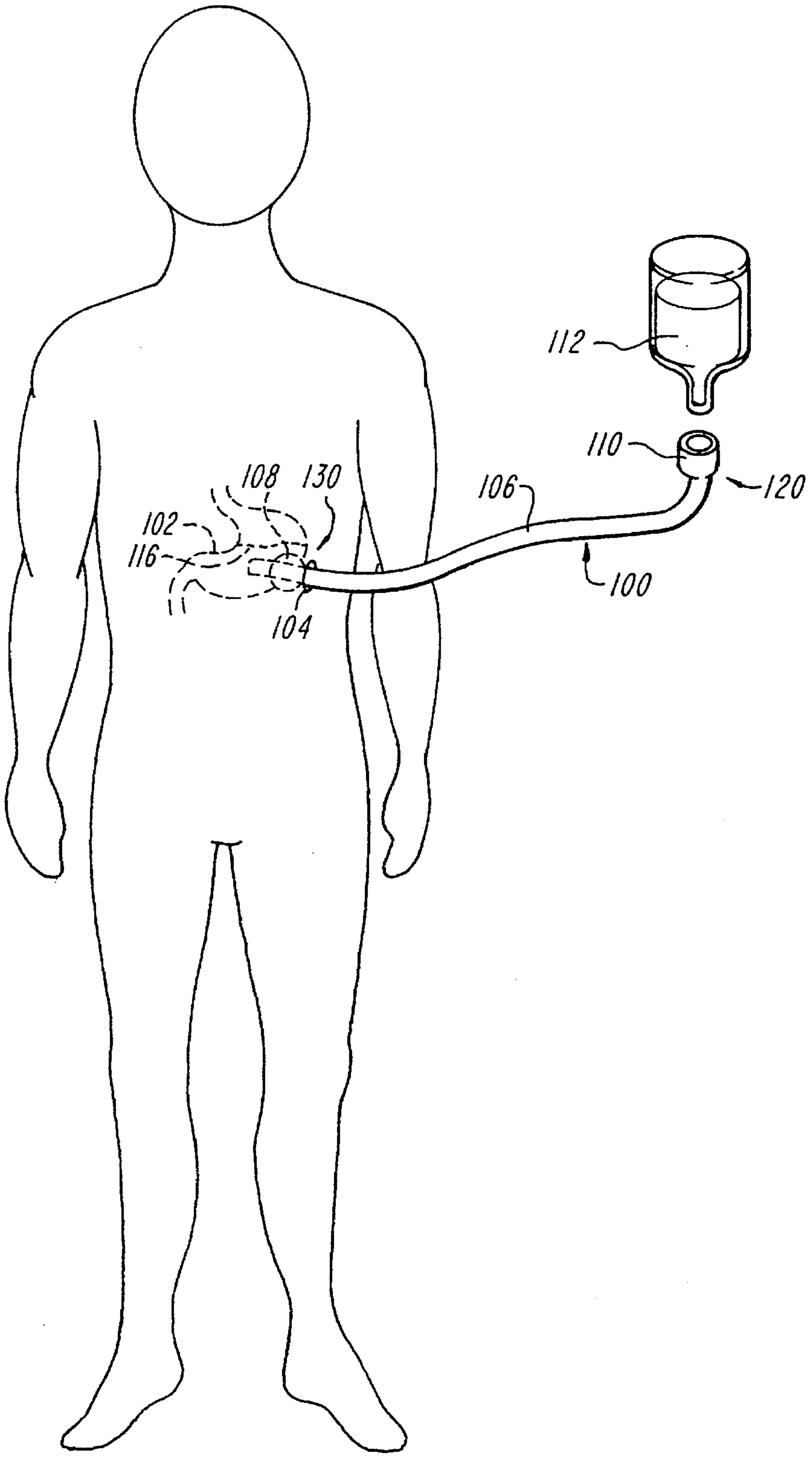
FIG. 1 (PRIOR ART)
FIG. 1 shows schematically a typical gastrological set-up of the prior art.

An embodiment of the invention is shown schematically with respect to FIGS. 2A and 2B. As with the prior art device, a tube 200 has a patient end 270, which is inserted through gastrostomy opening 104 and terminates in an anchor 108 of some sort, such as an inflated balloon. The anchor is, of course, devised to allow liquid, such as a nutrient from liquid source 112 to enter the patient's stomach 102 or other appropriate organ or body cavity. The end 260 of the tube that is distant from the patient and near to the liquid source 112 is referred to as the "source end" or "external end." It has a fitting 210 designed to engage the liquid source bottle 112, or a pump or syringe or other appropriate delivery apparatus. The type of fitting and delivery apparatus is not important to the invention, which is intended to operate with all such delivery apparatus and fittings.

Interposed between the source end 260 of the tube and the patient end 270 of the tube, is an anti-reflux valve 220, shown in an enlarged view in FIG. 2B. As discussed below the anti-reflux valve 220 can take many forms, and acts as a barrier to the flow of liquid in a direction from the patient toward the source bottle. For instance, as shown in FIG. 2B, a flapper 222 is hinged at 224. Flapper 222 is free to open in the direction indicated by arrow F, to allow liquid to flow in that direction, from the source to the patient. A stop 226 is positioned to prevent flapper 222 from opening in the reverse direction under elevated pressure toward the patient side of the valve, as compared to the source side of the valve. Thus, if pressure builds at the patient side, tending to urge liquid to flow back toward the source, flapper valve 222 closes against stop 226, which completely seals off the tube 200, thereby preventing any liquid from flowing from the patient toward the source.

Interposed between the anti-reflux barrier valve 220 and the patient end 270 of the tube 200 is a gas vent 230. The structure of the vent is discussed in more detail below. The vent 230 is designed to permit the flow of gas and vapor from within the tube 206 to the outside atmosphere, but to prevent the flow of liquid in the same direction. Thus, gasses that build up in the stomach or other organ or body cavity, and which flow toward the vent 230, can exit the tube 200 and stomach volume into the atmosphere, thus alleviating pressure to some degree.

In operation, then, at times of liquid introduction, such as feeding, the liquid source 112 is connected to tube 200 through connection 210 at the source end 200 of the tube. The liquid flows from the source toward the patient, passing through anti-reflux valve 220, which will be urged toward an open position due to the greater pressure at the source end 260 of the tube, relative to the pressure at the patient end 270. The liquid will pass by the vent 230, through tube 206 and into the patient, for instance, into the patient's stomach. If, during feeding, the pressure at the patient end 270 exceeds the pressure at the source end 260, backflow of liquid back through the tube and into source bottle 112, or out of connector 210 into the environment, is prevented due to anti-reflux valve 220. If the pressure is due to a build-up of gas, and if the gas makes its way to vent 230, the gas will leave the closed volume of the stomach and tube, into the atmosphere, thereby relieving the pressure.

During times when liquid is not intended to be introduced to the patient, but when it remains an object to prevent any back flowing liquid from contaminating the environment, the vent 230 allows "venting" of the patient. If the vent is maintained gravitationally above the patient's stomach, or other organ, etc., any gas in the stomach will pass through tube 206, encounter vent 230, and pass into the atmosphere, thereby relieving the pressure. This works similarly to the prior art, except that vent 230 is impervious to the backflow of liquid. Thus, it is not a great disaster if the vent falls gravitationally below the stomach, because the internal contents will not flow out of the vent or source end 260 into the atmosphere.

Figure 8A:
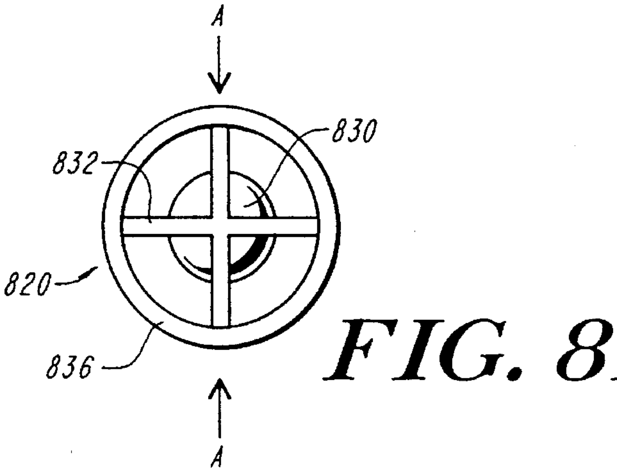
FIG. 8A shows an end view of an embodiment of the liquid reflux barrier portion of the invention.

The anti-reflux valve 220 may be of any suitable design that freely permits liquid to flow toward the patient and prevents liquid from flowing away from the patient, while satisfying the parameters of flow, sterilizability, simplicity, etc. For example, the valve can be a flapper valve, a ball valve, a float valve, etc. A flapper valve is shown in FIG. 2A, and a ball valve 820 is shown schematically in FIGS. 8A and 8B.

Figure 8B:
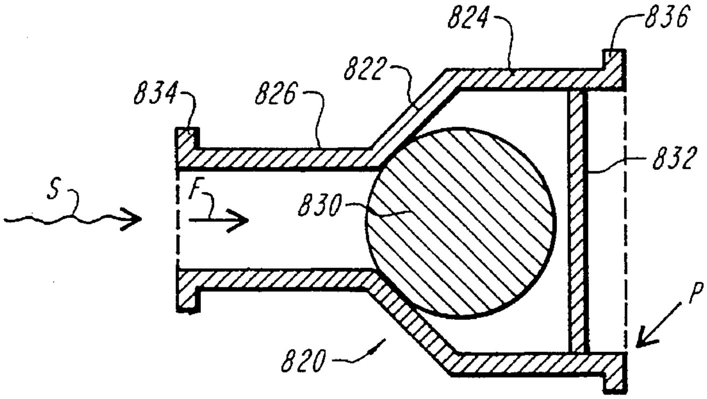
FIG. 8B shows the reflux barrier of FIG. 8A in cross-section along lines A—A.

FIG. 8B shows such a valve in cross-section. The body 822 of the valve has a portion of a relatively large diameter 824 and a portion of relatively small diameter 826, which portions are joined by a portion having a graduated diameter, from small to large, as going from the patient end P of the valve to the source end S. A ball 830 is captured between the inclined walls of graduated portion 828 and a cage 832. The ball is of sufficiently large diameter to completely close off the opening at the narrow end of the graduated section 828, when urged toward that end, but sufficiently small enough to permit substantial liquid flow in the direction from the source to the patient. Fittings 834 and 836 are provided at the source end and the patient end respectively, to allow connection of the anti-reflux valve 820 to the tube 206, which connects to the patient and to the tube 250, which connects to the source.

Figure 3A:
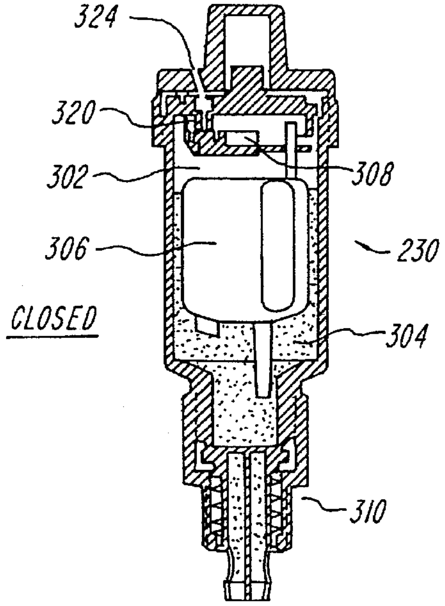
FIG. 3A shows in cross-section a vent valve that can be used as a component of the invention, in a position that is closed to liquid flow.
Figure 3B:
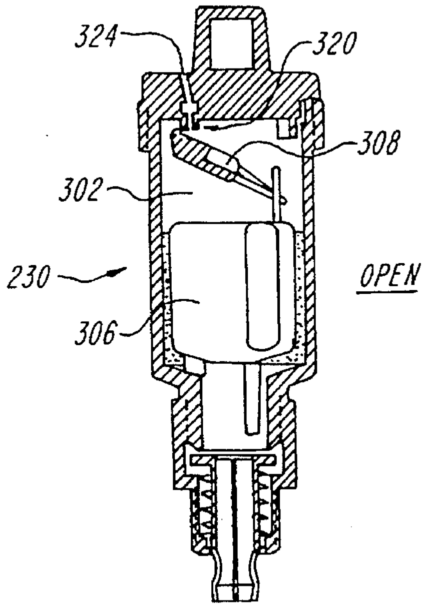
FIG. 3B shows in cross-section the vent valve of FIG. 3A in a position that is open to gas flow.

A gas vent suitable in function is shown schematically with respect to FIGS. 3A and 3B. This vent performs in the same fashion as does a vent on a radiator in a heating system for a building. Such vents are designed to permit steam and air to leave the piping circuit, but to prevent water from leaving the circuit. When there is less than a certain volume of air or steam in vent cavity 302, liquid 304, enters the vent, causing the float 306 to become buoyant and to move toward the air release valve 308. This closes the opening 320, preventing the emission of any gas or liquid through channel 324. A small quantity of gas may be retained within vent cavity 302 to provide a gas cushion that protects the air release valve against liquid spray.

The situation when gas is present in the vent is shown in FIG. 3B. The float 306 descends within the body of the vent, thus clearing the opening 320, enabling any accumulated gas to escape through channel 324. The quantity of gas which is released depends on the relative pressures.

According to one embodiment of the invention, the vent assembly has a fitting neck 310, adapted to be easily attached and detached to a mating fitting 252 that is attached to tube 206. The vent may then be installed during feeding, or when venting is needed. At other times, the Y branch in the tubing 206 can be used for flushing, applying medications, etc.

Many other types of vents can be used. What is required is that the vent allow gas to escape, but prevent liquid from escaping. Another type of device that is also suitable for incorporation into the invention is shown with reference to FIGS. 4, 5, 6 and 7.

Figure 4:
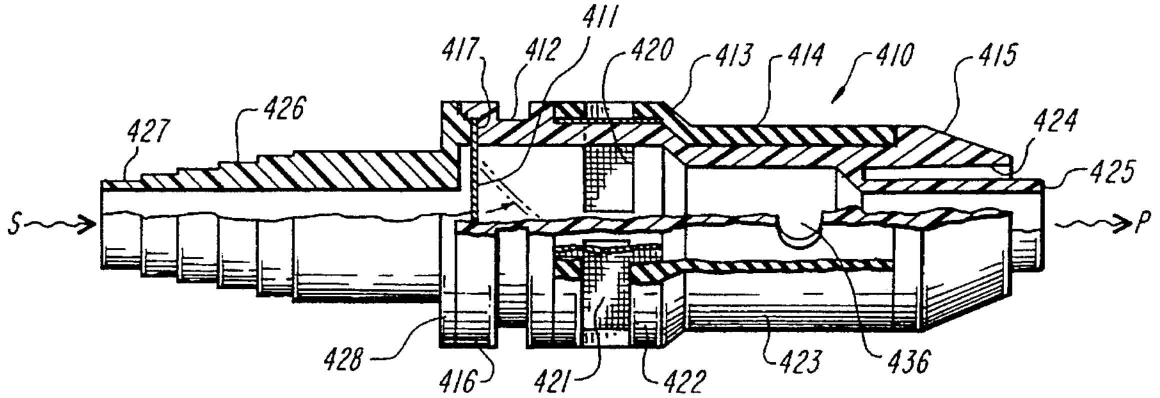
FIG. 4 shows in partial cross-section an embodiment of a portion of the invention, having a unitary reflux barrier and gas vent structure.
Figure 5:
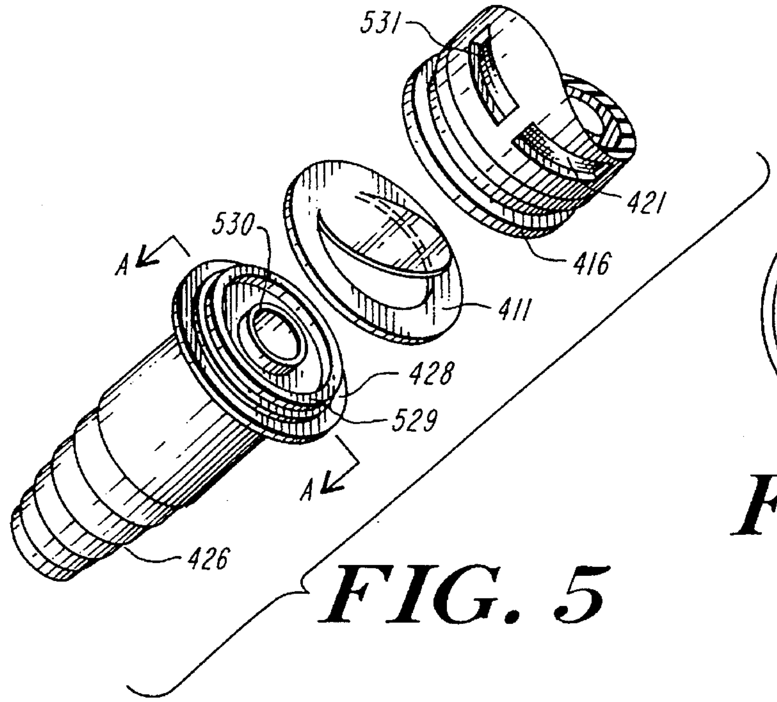
FIG. 5 shows a portion of the unitary embodiment of the invention shown in FIG. 4, in a partially exploded view.
Figure 6:
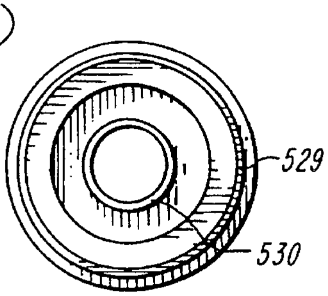
FIG. 6 shows a portion of an element shown in exploded view in FIG. 5, as viewed along arrows A—A.

The device shown in FIGS. 4–7 is a unitary assembly having a valve and a vent. As shown in FIG. 4, the unitary assembly is installed with appropriate tubing, aligned with the end identified S toward the source and the end identified P toward the patient. The unitary assembly includes a tubular body 410, having a having a source end 412, a first intermediate section 413 adjacent the source end 412 and a second intermediate section 414 adjacent patient end 415. The source end 412 is formed with a flange 416 having a circumferential recess 417 formed therein, adapted to receive and support a valve 411.

Figure 7:
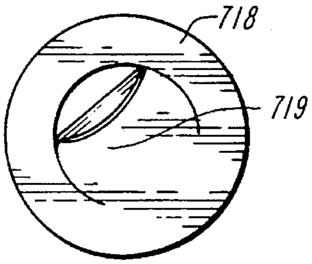
FIG. 7 is an elevation view of a valve disc of the portion of the invention shown in exploded view in FIG. 5.

Valve 411 is a disc shaped member having (as shown in FIG. 7) a main body portion 718 with a C shaped slice formed therein, thus forming flap 719. Valve 411 may be fabricated from a polyester, such as MYLAR, a trademark of DuPont DeNemours and Company. First intermediate section 413 defines vent openings 420 and supports vent fabric 421. Vent fabric 421 is shaped in a ring surrounding section 413 and is made from a semipermeable fabric. The fabric is permeable to air and gas and water vapor but not to liquid water. A suitable fabric for such use is a polytetrafluoroethylene fabric having interconnected pores of about 0.45 microns, such as sold under the tradename Goretex, by the William L. Gore company of Elkton, Md. The fabric ring is slipped over intermediate section 413 and held in place by retainer 422, which defines openings 531, corresponding to openings 420.

Patient end section 415 has an inner surface 424 and an inner tubular member 425, which preferably extends past the end of surface 424. The space defined by surface 424 and the outside of tubular member 425 receives tubing such that the tubing wall surrounds member 425. Such tubing extends from the unitary unit toward the patient.

A tube connector cap 426 is provided for attachment at the source end of assembly 410 and attachment to tubing from the liquid source, such as a nutrient. Cap 426 terminates in a graduated tubing connector end 427 and flange 428. Raised rib 529 (FIG. 5) on flange 428 cooperates with recess 417 on flange 416 and retains valve 411 therein and aligns cap 426 with tubular body 410. Rib 530 is concentric with and of lesser diameter than rib 529 and provides a seat for valve 411.

Tubular body 410 may be molded by a single conventional operation to include vent holes 420. Then ring 421 is slipped over intermediate portion 413 and a second molding operation is performed to fabricate retention sleeve 422. Finally, the polyester valve 411 is placed on the end of the tubular housing and tube connector cap 426 is ultrasonically bonded to body 410. Disc 411 is effectively retained therebetween.

In operation, if liquid is to be introduced to the patient, it is presented to the source end of the assembly, and forces flap 719 into the open position. Liquid flows by the open flap 719, and the internal chambers of the unit and out through the patient end 415, toward the patient. If the pressure on the patient side of the unit increases relative to the source side, the flapper valve 719 closes, thereby preventing liquid backflow. If air or other gas is present in the line, it may pass through semi-permeable membrane 421 to the atmosphere, while liquid is retained within the apparatus. Thus, the patient may be vented without any potential for contamination of the environment.

The invention has been described particularly in connection with providing nutrients to a patient's stomach, through a gastrostomy. The invention can also be used in connection with a nasogastric tube, introduced through the patient's nose, rather than a surgical opening, such as a gastrostomy. The invention also relates to introducing medicine, analytical agents, such as dyes or radioactive markers, to the stomach, or any other suitable body cavity. Animal as well as human patients are suitable subjects for use of the invention. The invention has been described in connection with separate and unitary combinations of the anti-reflux valve and the vent valve. Further, the two types of valves may be formed integrally with the tube through which the liquid flows from the source to the patient. Alternatively, the valves may be separate from the tube, which may take the form of several separate segments, joined to the valves through fittings designed for that purpose. The liquid may be provided under the influence of a pump, gravity or a combination thereof, as well as using a syringe.

The foregoing discussion should be understood as illustrative and should not be considered to be limiting in any sense. While this invention has been particularly shown and described with references to preferred embodiments thereof, it will be understood by those skilled in the art that various changes in form and details may be made therein without departing from the spirit and scope of the invention as defined by the claims.

Having described the invention, what is claimed is:

1. A method for administering liquid nutrient to the digestive tract of a living mammalian subject, said method comprising the steps of:

a. introducing one end of a tube into said digestive tract of the subject, leaving the other end of the tube free;

b. providing an apparatus comprising:

i. a body portion, having:

(a). a subject end, having means for hydraulically connecting to the free end of said tube;

(b). a liquid supply end, having means for engaging a liquid supply; and (c). a lumen portion connecting said subject end to said liquid supply end;

ii. valve means, located hydraulically between said subject end and said liquid supply end for allowing liquid to pass in the direction from the liquid supply end toward the subject end and for preventing liquid from passing from the subject end to the liquid supply end; and iii. located between the valve means and the subject end, vent means for permitting gas to exit the body portion and for preventing liquid from exiting the body portion other than through said subject end;

c. connecting said subject end of said apparatus to said free end of said tube;

d. introducing liquid nutrient into said apparatus at said liquid supply end, whereby said liquid is free to pass from said liquid supply end toward the subject, while any liquid urged to pass from the subject end toward the liquid supply end is prevented from passing away from the subject beyond the valve means and whereby gas urged to pass away from the subject exits the apparatus from the vent means, and whereby liquid is prevented from exiting the apparatus through the vent means.

2. The method of claim 1, where said step of introducing one end of a tube into said digestive tract of the subject, comprises the step of introducing said tube into said subject's stomach.

3. The method of claim 1, where said step of introducing said tube into said subject's digestive tract comprises the step of introducing said tube through an incision in the stomach wall.

4. The method of claim 1, where said step of introducing said tube into said subject's digestive tract comprises the step of introducing said tube through the subject's nasal passage.

* * * * *